United States Patent [19]

Higo

[11] Patent Number: 4,728,500

[45] Date of Patent: Mar. 1, 1988

[54] STIRRER FOR BIOCHEMICAL REACTIONS
[75] Inventor: Yuji Higo, Nagoya, Japan
[73] Assignee: Toyo Soda Manufacturing Co., Ltd., Shinnanyo, Japan
[21] Appl. No.: 893,620
[22] Filed: Aug. 6, 1986
[30] Foreign Application Priority Data Aug. 7, 1985 [JP] Japan ............................... 60-173896

[51] Int. Cl.⁴ ...................... B01F 13/08; G01N 33/543
[52] U.S. Cl. ........................................ 422/99; 422/71; 422/73; 422/224; 436/518; 366/274
[58] Field of Search ...................... 422/69, 71, 73, 99, 422/224; 436/518; 366/273, 274

[56] References Cited

U.S. PATENT DOCUMENTS

| | | | |
|---|---|---|---|
| 3,997,272 | 12/1976 | George | 366/274 X |
| 4,067,959 | 1/1978 | Bolz | 422/69 X |
| 4,200,613 | 4/1980 | Alfrey et al. | 422/71 |
| 4,568,192 | 2/1986 | Kudermann et al. | 366/146 |

FOREIGN PATENT DOCUMENTS 1251277 10/1967 Fed. Rep. of Germany .
0032416 8/1980 Japan .
0197708 9/1977 U.S.S.R. .

Primary Examiner—Michael S. Marcus
Assistant Examiner—Lynn M. Kummert
Attorney, Agent, or Firm—Oblon, Fisher, Spivak, McClelland & Maier

[57] ABSTRACT

A stirrer for biochemical reactions comprising a magnetically permeable vessel for containing a solution of biochemically reacting substances, at least one magnetic bead placed in the vessel, and a magnetic device which is installed outside the vessel and generates an oscillating magnetic field acting on the bead. The stirrer is advantageous for stirring the solution of biochemically reacting substances for biochemical reactions without direct contact.

4 Claims, 3 Drawing Figures

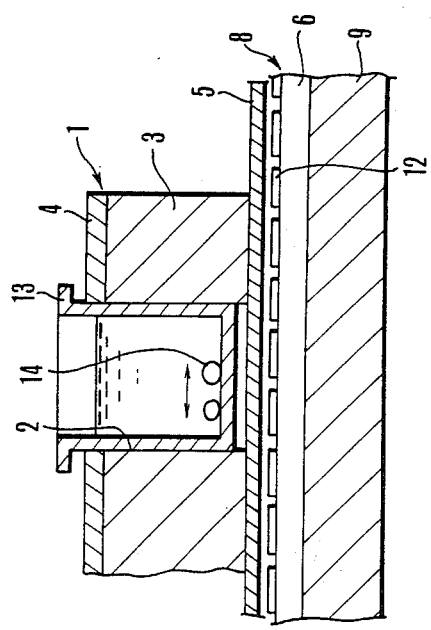
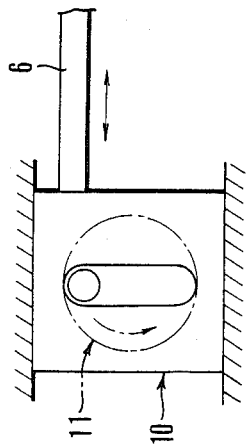
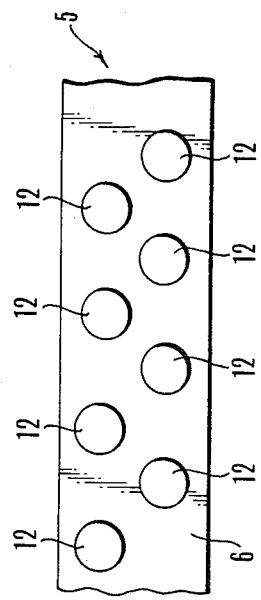
FIG.2(a)
FIG.2(b)

STIRRER FOR BIOCHEMICAL REACTIONS

BACKGROUND OF THE INVENTION

Field of the Invention

The present invention relates to an apparatus for biochemical reactions, and more particularly to an apparatus which permits adequate agitation of solutions that undergo biochemical reactions.

Following description is made with reference to an apparatus for immunological reactions by which the present invention can be most appropriately practised. In the immunological reactions, either the antigen or the antibody is marked with a convenient label (for example, a fluorescent or radioactive material or an enzyme) and the immunological reaction is utilized to form a complex body of the antigen and the antibody. The antibody having the label in it gives a measure to estimate the amount of the object antigen or antibody.

For the reaction to proceed adequately, to increase the accuracy and precision of estimation, to carry out the process more rapidly, and to enhance the efficiency of operations, the procedure of stirring is preferable as it is in most chemical reactions.

However, in biochemical reactions such as immunological reaction where a small volume of sample, say from several hundreds microliters to several tens milliliters, is commonly employed, difficulties are often met in agitating the solution. A stirrer with blades cannot be used practically and, if the stirring means is brought into contact with the solution, the the estimation may bring about loss in accuracy probably due to "carry over". Stirring by oscillating the vessel itself cannot be expected to be effective and loss of the solution by spattering is feared. Stirring by ultrasonic waves as non-contact stirring may cause the reacting substances to be destroyed and therefore is not universally applicable.

SUMMARY OF THE INVENTION

To solve the above-mentioned problems, an object of the present invention is to provide an apparatus by which a solution containing biochemically reactive substances is stirred efficiently without direct contact.

Another object of this invention is to provide a versatile stirring apparatus which does not adversely affect the reacting substances involved.

DETAILED DESCRIPTION OF THE INVENTION

The stirrer for biochemical reactions provided by the present invention which has been made to attain the aims mentioned above comprises a magnetically permeable vessel for containing a solution of biochemically reacting substances, at least one magnetic bead placed in the vessel, and a magnetic device which is installed outside the vessel and generates an oscillating magnetic field acting on the bead.

The magnetically permeable vessel of this invention may be in the form of a cup, a plate having a number of concavities where reactions take place, a column and any other suitable design, and can be made of a magnetically permeable material such as glass, resins, etc.

The magnetic bead to be placed in the vessel may include a magnet, per se, magnetic powders conglomerated by a resin binder, a bead which is surface coated by a suitable material and others. The dimension depends on the size and shape of the vessel, but generally a diameter of 0.5–10 mm is preferred. One to several beads may be used for the purpose.

Further, it is preferred for immunological reaction to fix an antibody on the surface of the magnetic beads, so as to form an insoluble carrier of the antibody.

The magnetic device is intended to move the magnetic beads to oscillate (in an alternating or a circular movement) themselves in the vessel with a predetermined frequency, and the oscillation may be performed at a low frequency ranging from 10 to 120 per min. as considered appropriate to the aim of the stirring. The oscillating field provided by the magnetic device may be produced by a coil in which an alternating current flows and by a movement (alternating or circular) of a permanent magnet. In considering the heating effect, the latter method, or use of a permanent magnet, is more often preferred.

The biochemical reactions to which the stirrer of this invention can be used with merit include immunological, enzymatic and agglutination reactions. But the invention is not particularly restricted to any of the cited examples.

BRIEF DESCRIPTION OF THE DRAWINGS

FIG. 2(a) is a cross-section of the magnetic device and

FIG. 2(b) is a plan of one of the magnetic bars.

DETAILED DESCRIPTION OF THE PREFERRED EMBODIMENTS

Figure 1:
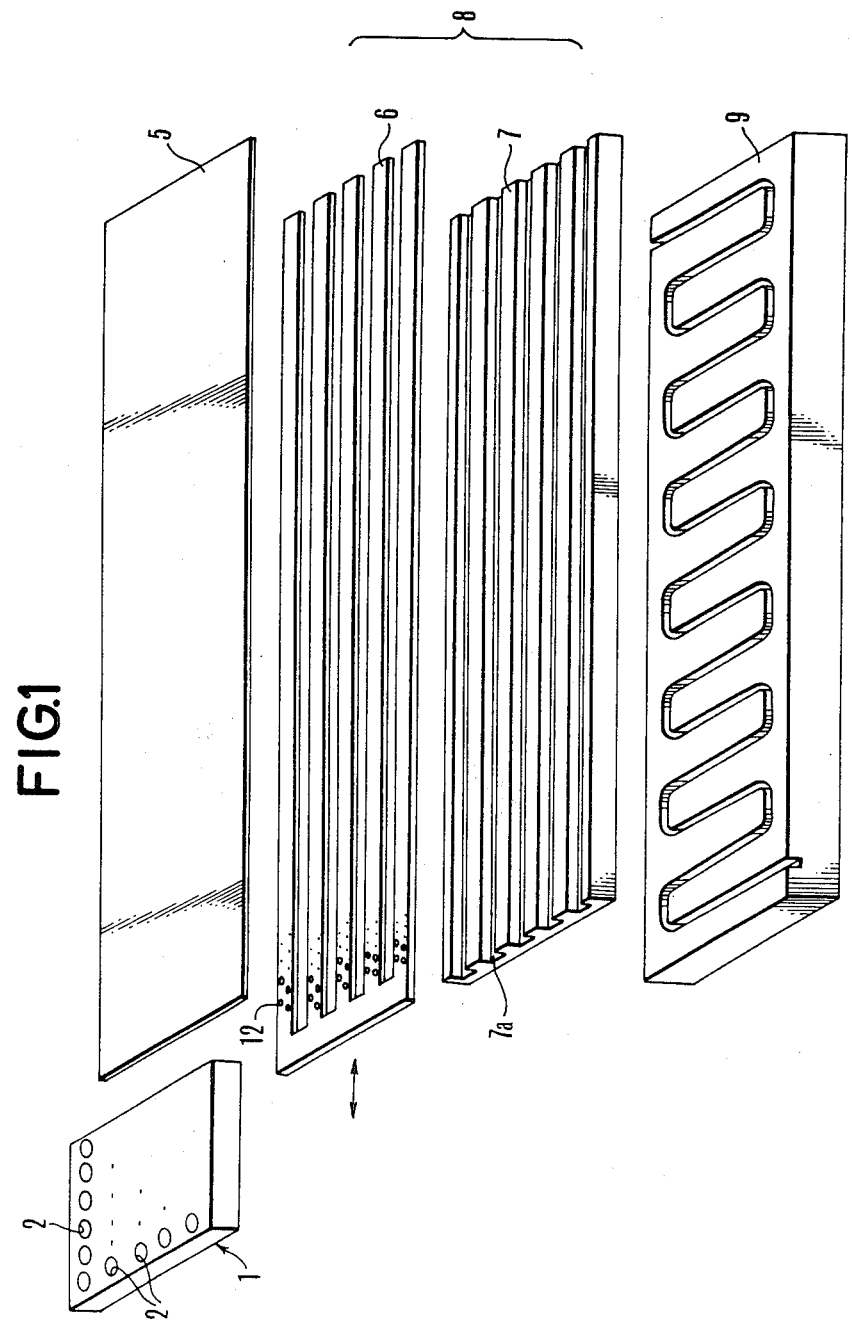
FIG. 1 is a developed drawing showing the constitutional outline of the stirrer of the present invention.

The present invention will be described referring to the accompanying drawings.

FIG. 1 is a developed graphical representation showing the outline of the stirring apparatus, where 1 is a test plate on which a plurality (5×6) of circular openings 2, each to incorporate a test cup 13, are provided. As shown in FIG. 2, the test plate is made of an aluminum plate 3, aluminum being a magnetically permeable substance, on the upper surface of which is intimately attached a thin plate of a resin 4 to suppress the dissipation of heat.

The lamination structure of 5, 8 and 9 forms a setting stage for the test plate 1 (or serves as a carrying stage when combined with a suitable transportation means), where 5 is an upper cover plate, 8 is a magnetic device, and 9 is a thermostat.

The magnetic device 8 is composed of a spacer 7 which has along the surface a number of longitudinal ditches 7a parallel to each other and magnetic bars 6 which are placed in the ditches of 7a one by one. The magnetic bars 6 are capable of moving in the longitudinal direction and their one ends are consolidated outside of the spacer 7 and the whole can be moved back and forth with a definite amplitude in the longitudinal direction by the action of an eccentric cam mechanism 10 and a driving motor 11. On the upper side (facing to the upper cover plate 5) of the magnetic bars 6, a number of circular pieces of magnet 12 are fixed alternatively as indicated in FIG. 2(b), and they apply a magnetic field on the magnetic beads 14 in the test cups 13.

In this configuration described above, the magnetic beads 14 in the test cups 13 are influenced by the oscillating magnetic field, as the magnetic bar 6 moves back and forth, to move in the solution, and hence non-contact agitation is realized. In this example, pieces of magnet 12 are arranged in two rows and the pitch in each row is nearly equal to the diameter of the test cups, so that the magnetic beads undergo an elliptic motion.

The above-mentioned stirrer for biochemical reactions according to the present invention permits an effective stirring of a solution to be realized in a relatively small vessel in a non-contact manner and an improvement lies in the fact that the degree of agitation can be varied by simply adjusting the magnetic device. Thus, good utility is expected by using the apparatus according to the present invention.

Since the performance is made by use of the magnetic device which is placed close to the vessels, any operation to be made to the vessels when necessary, for instance, placing a sample solution in a vessel and conducting an optical measurement, is possible without trouble.

What is claimed is:

1. A stirrer for biochemical reactions, comprising:
   at least one vessel formed of magnetically permeable material for containing a solution of a biochemically reactive substance;
   at least one magnetic bead positionable in each said at least one vessel;
   means for generating a regularly oscillating magnetic field in each said at least one vessel for oscillating said at least one bead, said generating means comprising a bar having pieces of magnet implanted thereon and positioned relative to said at least one vessel so as to magnetically affect said at least one bead in said at least one vessel, and drive means for regularly oscillating said bar, whereby said at least one bead is regularly oscillated.

2. The stirrer of claim 1 including means for supporting a plurality of said vessels, wherein said bar comprises a plurality of commonly connected bar portions, each of said bar portions extending beneath at least one of said vessels supported by said supporting means.

3. The stirrer of claim 1 including an antibody fixed on said at least one bead, whereby said at least one bead comprises an insoluble carrier of said antibody.

4. The stirrer of claim 3 including means for supporting a plurality of said vessels, wherein said bar comprises a plurality of commonly connected bar portions, each of said bar portions extending beneath at least one of said vessels supported by said supporting means.

* * * * *